United States Patent
Komorowski

(10) Patent No.: US 11,246,886 B2
(45) Date of Patent: *Feb. 15, 2022

(54) TREATMENT OF AUTISM AND AUTISM SPECTRUM DISORDERS WITH BIOTIN COMPOSITIONS

(71) Applicant: NUTRITION 21, LLC, Harrison, NY (US)

(72) Inventor: James R. Komorowski, Trumbull, CT (US)

(73) Assignee: NUTRITION 21, LLC, Harrison, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/560,826

(22) Filed: Sep. 4, 2019

(65) Prior Publication Data

US 2020/0078394 A1 Mar. 12, 2020

Related U.S. Application Data

(60) Provisional application No. 62/727,861, filed on Sep. 6, 2018.

(51) Int. Cl.
*A61K 33/06* (2006.01)
*G01N 33/50* (2006.01)

(52) U.S. Cl.
CPC ......... *A61K 33/06* (2013.01); *G01N 33/5008* (2013.01)

(58) Field of Classification Search
CPC .............. A61K 33/06; G01N 33/5008; G01N 2800/30; G01N 33/5308; G01N 33/56972
See application file for complete search history.

(56) References Cited

U.S. PATENT DOCUMENTS

| 6,709,868 B2 | 3/2004 | Law et al. | |
| 2007/0020206 A1* | 1/2007 | Jermann | A61K 31/4188 424/62 |
| 2009/0104171 A1* | 4/2009 | Pardee | A61P 25/24 424/94.1 |

FOREIGN PATENT DOCUMENTS

WO WO-2018/045244 A1 3/2018

OTHER PUBLICATIONS

Spillioti et al. (Frontiers in Human NeuroScience, Dec. 24, 2013, vol. 7) (Year: 2013).*
Adams et al. (Nutrition & Metabolism, 2011, 8:34, 1-32) (Year: 2011).*
Deans (https://www.psychologytoday.com/us/blog/evolutionary-psychiatry/201402/targeted-diet-interventions-in-autistic-spectrum-disorders-0, 2014, pp. 1-2) (Year: 2014).*
Simons (Eur Child Adolesc Psychiatry, 2017, 26:143-154) (Year: 2017).*
Adams et al., "Effect of a vitamin/mineral supplement on children and adults with autism," BMC Pediatrics, Dec. 2011; 11(111), [retrieved on Oct. 8, 2019]. Retrieved from the Internet: <URL: https://bmcpediatr.biomedcentral.com/track/pdf/10.1186/1471-2431-11-111>.
International Search Report and Written Opinion issued in connection with PCT/US2019/049915, dated Nov. 12, 2019.
U.S. Department of Health and Human Services, FDA, "Guidance for Industry: Q3C Impurities: Residual Solvents," Dec. 1997.
University of California—Davis Health System. "Children with autism have mitochondrial dysfunction, study finds." ScienceDaily, Nov. 30, 2010 [retrieved on Oct. 18, 2019]. Retrieved from the Internet: <https://www.sciencedaily.com/releases/2010/11/101130161521.htm>.

* cited by examiner

*Primary Examiner* — Umamaheswari Ramachandran
(74) *Attorney, Agent, or Firm* — Arnall Golden Gregory LLP

(57) ABSTRACT

The present application relates to the treatment of autism and autism spectrum disorders using biotin compositions.

14 Claims, No Drawings

TREATMENT OF AUTISM AND AUTISM SPECTRUM DISORDERS WITH BIOTIN COMPOSITIONS

CROSS-REFERENCE TO RELATED APPLICATIONS

This application claims priority to of U.S. Provisional Application No. 62/727,861 filed Sep. 6, 2018, the contents of which is incorporated by reference herein in its entirety.

BACKGROUND

Field

The present application relates to the treatment of autism and autism spectrum disorders with biotin compositions.

Description of the Related Art

Biotin is an essential water-soluble vitamin also known as Vitamin H, Coenzyme R, and Vitamin B7. It is an essential co-factor for five known carboxylases involved in fatty acid biosynthesis, gluconeogenesis, branched-chain amino acid metabolism, fatty acid metabolism, tricarboxylic acid cycle anaplerosis, and pleiotropic gene regulation, particularly for genes in carbohydrate metabolism. Magnesium biotinate is more water soluble than biotin.

Autism, or autism spectrum disorder, is used to refer to a range of conditions characterized by challenges with social skills, repetitive behaviors, speech and nonverbal communication. Individuals with an autism spectrum disorder are usually diagnosed between 2 and 3 years of age. In some cases, it can be diagnosed as early as 18 months. Some developmental delays associated with autism can be identified and addressed even earlier. Some metabolic disorders have been associated with autism.

SUMMARY OF THE INVENTION

In some embodiments, biotin can be used to treat an autism spectrum disorder. In some embodiments, a biotin salt can be used to treat an autism spectrum disorder. In some embodiments magnesium biotinate can be used to treat an autism spectrum disorder. In some embodiments, the type of autism spectrum disorder to be treated may differ. In some embodiments, the type of autism spectrum disorder to be treated may be related to low biotin levels, impaired carboxylase function, increased propionic acid levels, or increased levels of isoleucine, methionine, threonine, and/or valine. In some embodiments, the amount of biotin or biotin salt administered is between 10 mg/day to 10000 mg/day. In some embodiments, the amount of biotin or biotin salt administered is between 100 mg/day and 1000 mg/day. In some embodiments, the biotin, biotin salt, or magnesium biotinate can be administered once a day. In some embodiments, the biotin, biotin salt, or magnesium biotinate can be administered more than once a day. In some embodiments, the biotin, biotin salt, or magnesium biotinate can be administered via an oral route. In some embodiments, the biotin, biotin salt, or magnesium biotinate can be administered via an intraperitoneal route. In some embodiments, the biotin, biotin salt, or magnesium biotinate can be administered via a transdermal, rectal, or sublingual route. In some embodiments, the amount of magnesium biotinate administered is between 10 mg/day to 1000 mg/day. In some embodiments, the amount of magnesium biotinate administered is between 10 mg/day and 100 mg/day. In some embodiments, the biotin, biotin salt, or magnesium biotinate can be provided as a drug, supplement, medical food, food or biologic. In some embodiments, the biotin, biotin salt, or magnesium biotinate is administered alone. In some embodiments, the biotin, biotin salt, or magnesium biotinate is administered in combination with another treatment. In some embodiments, the biotin, biotin salt, or magnesium biotinate is administered for 1 or more days. In some embodiments, the biotin, biotin salt, or magnesium biotinate is administered for 1 or more weeks. In some embodiments, the biotin, biotin salt, or magnesium biotinate is administered for 1 or more months. In some embodiments, the biotin, biotin salt, or magnesium biotinate is administered for 1 or more years. In some embodiments, the biotin, biotin salt, or magnesium biotinate is administered to a pregnant woman or to a woman attempting to become pregnant to prevent a child from developing autism. In some embodiments, the amount of biotin, biotin salt, or magnesium biotinate administered to the pregnant woman may be the same throughout the pregnancy. In some embodiments, the amount of biotin, biotin salt, or magnesium biotinate administered to the pregnant woman may differ in each trimester. In some embodiments, the amount of biotin, biotin salt, or magnesium biotinate administered to the pregnant woman may be higher during the second trimester.

In some embodiments, the invention provides a method of treatment comprising assessing the biotin status of an individual with an autism spectrum disorder and subsequently providing biotin, biotin salt, or magnesium biotinate to the individual to treat the autism spectrum disorder. In some embodiments, assessing the biotin status of the individual with an autism spectrum disorder comprises obtaining samples from the individual and testing for markers associated with biotin deficiency. In some embodiments, the samples are obtained from blood, serum, peripheral blood mononuclear cell (PBMC), saliva, urine, feces or sweat from the individual with an autism spectrum disorder. In some embodiments, the samples can be tested for markers indicative of impaired carboxylases. In some embodiments, the samples can be tested for impaired propionyl-CoA carboxylase (PCC) or pyruvate carboxylase (PC). In some embodiments, the samples can be tested for amino acids found at abnormal levels due to impaired PCC or PC or other carboxylase. In some embodiments, the samples can be tested for biotin, propionic acid, pyruvate, or lactate. In some embodiments, the samples can be tested for isoleucine, methionine, threonine, and valine. In some embodiments, the samples can be tested for ratios of one amino acid over another. In some embodiments, the samples can be tested for white blood cell count. In some embodiments, the samples can be tested for mitochondrial function.

DETAILED DESCRIPTION

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, "treat," "treatment," or "treating," refers to administering or providing a composition for prophylactic and/or therapeutic purposes.

As used herein, the terms "prophylactic treatment," "prevent," or "preventing," can refer to treating a subject who does not yet exhibit symptoms of a disease or condition, but who is susceptible to, or otherwise at risk of, a particular disease or condition, whereby the treatment reduces the likelihood that the subject will develop the disease or condition. A "disorder" is any condition that would benefit from treatment with the compositions described herein.

The term "biotin" means D-biotin, an essential water-soluble vitamin also known as Vitamin H, Coenzyme R, or vitamin B7. D-Biotin has Chemical Abstracts Service Registry No. 58-85-5 and the general formula:

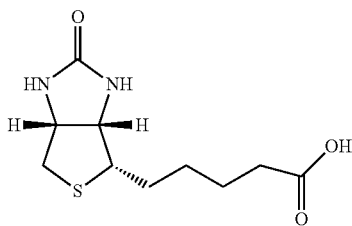

As used herein, the term "biotin salt" refers to an organic, or inorganic salt of D-biotin. Typical salts include alkali metal, alkaline earth metal, ammonia, or organic amine salts as, for example, sodium, potassium, magnesium, calcium, protonated amines such as those derived from ethylamine, triethylamine, ethanolamine, diethylamino-ethanol, ethylenediamine, piperidine, morpholine, 2-piperidinoethanol, benzylamine, procaine and the like As used herein, the term "magnesium biotinate" refers to the magnesium salt of D-biotin, including magnesium hemi-biotinate. Magnesium D-biotinate is the magnesium salt of the carboxylic acid D-biotin, and does not occur naturally. In some embodiments, magnesium D-biotinate is a stable, non-hygroscopic, off-white powder having a defined composition, a molecular formula of $Mg(C_{10}H_{15}N_2O_3S)_2$ and a general formula of

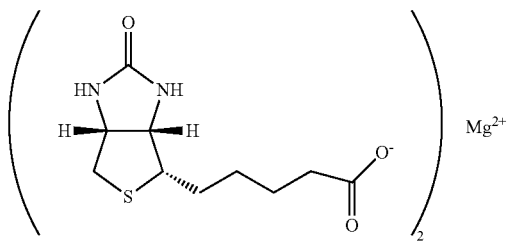

Some embodiments provide physiologically compatible magnesium biotinate hydrates, crystalline forms, polymorphic forms, solid forms having specific bulk densities or tap densities, and solid forms having specific particle sizes. Some embodiments provide compositions coated with pharmaceutically acceptable materials intended to modify its release and/or bioavailability, including, but not limited to Eudragit, microcrystalline cellulose, hydroxypropylmethylcellulose phthalate, and the like.

As used herein, the term "magnesium" refers to the magnesium ion, $Mg^{2+}$.

As used herein, the term "pharmaceutically acceptable solvent" can refer to water, water for injection, aqueous buffer solutions that are physiologically compatible, or aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents," December 1997 or its current issue.

As used herein, the term "bioavailability" refers to the amount of a substance that is absorbed in the intestines and ultimately available for biological activity in a subject's tissue and cells.

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

For oral administration, the compositions disclosed herein can be provided as a tablet, aqueous or oil suspension, dispersible powder or granule, emulsion, hard or soft capsule, syrup, elixir, or beverage. Solid dosage forms such as tablets and capsules may comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin-containing or non-gelatinous capsules wherein the biotin, biotin salt, or magnesium biotinate is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the complex of the biotin, biotin salt, or magnesium biotinate admixed with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the biotin, biotin salt, or magnesium biotinate in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules suitable for preparation of an aqueous suspension by the addition of water can provide the biotin, biotin salt, or magnesium biotinate in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

Compositions for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

Aqueous suspensions may contain the biotin, biotin salt, or magnesium biotinate in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Controlled release vehicles are well known to those of skill in the pharmaceutical sciences, and these aspects can be applied to nutritional and dietary supplements. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, are also well known and can be used in the disclosed methods.

Controlled release preparations can be achieved by the use of polymers to form complexes with or absorb the biotin, biotin salt, or magnesium biotinate. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of biotin, biotin salt, or magnesium biotinate.

Controlled release of biotin, biotin salt, or magnesium biotinate can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein biotin, biotin salt, or magnesium biotinate is dissolved in an aqueous constituent to gradually release over time, can be prepared by copolymerization of hydrophilic mono-olefinic monomers such as ethylene glycol methacrylate. Matrix devices, wherein biotin, biotin salt, or magnesium biotinate is dispersed in a matrix of carrier material, can be used. The carrier can be porous, non-porous, solid, semi-solid, permeable or impermeable. Alternatively, a device comprising a central reservoir of magnesium biotinate surrounded by a rate controlling membrane can be used to control the release of the complex. Rate controlling membranes include ethylene-vinyl acetate copolymer or butylene terephthalate/polytetramethylene ether terephthalate. Use of silicon rubber or ethylene-vinyl alcohol depots are also contemplated.

Controlled release oral formulations are also well known. In one embodiment, the active complex is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

Biotin, biotin salt, or magnesium biotinate may also be delivery topically, including in a salve, cream, lotion, ointment, shampoo, cosmetic, or emulsion.

The compositions may be administered once, twice, three times per day, or more. In some aspects, the compositions are administered four times a day. For example, the compositions may be administered before, after, or during a meal. Dosing for oral administration may be with a regimen calling for single daily dose, or for a single dose every other day, or for a single dose within 72 hours of the first administered dose, or for multiple, spaced doses throughout the day. In some embodiments, wherein biotin, a biotin salt, or magnesium biotinate is combined with another treatment in a combination therapy, the biotin, biotin salt, or magnesium biotinate and the other active agents which make up the combination therapy may be administered simultaneously, either in a combined dosage form or in separate dosage forms intended for substantially simultaneous oral administration. The biotin, biotin salt, or magnesium biotinate and the other active agents which make up the combination therapy may also be administered sequentially, with either the biotin, biotin salt, or magnesium biotinate and the other active component being administered by a regimen calling for two-step ingestion. Thus, a regimen may call for sequential administration of the biotin, biotin salt, or magnesium biotinate and the other active agents with spaced-apart ingestion of the separate compositions. The time period between the multiple ingestion steps may range from a few minutes to as long as about 72 hours, depending upon the properties of each composition such as potency, solubility, bioavailability, plasma half-life and kinetic profile of the agent, as well as depending upon the age and condition of the patient. The compositions of the combination therapy, i.e., biotin, biotin salt, or magnesium biotinate and the other active agents, whether administered simultaneously, substantially simultaneously, or sequentially, may involve a regimen calling for administration of one composition by oral route and the other composition by intravenous route. Whether the compositions of a combined therapy are administered by oral or intravenous route, separately or together, each such composition will be a suitable pharmaceutical formulation of pharmaceutically-acceptable excipients, diluents or other formulations components.

Active ingredients (e.g., biotin, biotin salt, or magnesium biotinate and the other active ingredients of a combination therapy) can be administered by the oral route in solid dosage forms, such as tablets, capsules, and powders, or in liquid dosage forms, such as elixirs, syrups, and suspensions. The biotin, biotin salt, or magnesium biotinate and the other active ingredients of a combination therapy can be administered by the parenteral route in liquid dosage forms. The composition can be made in the form of a dosage unit containing a particular amount of each active ingredient. One example of an oral dosage form of a composition of the present application is an admixture of powders contained within a sachet. Because a composition of the present application is not hygroscopic and has no repugnant taste or odor, the admixture of powders comprising a composition of the present application can be sprinkled on food or stirred into beverages to enhance ease of use and support high levels of compliance with daily dosage regimens.

In general, the dosage forms of compositions of this disclosure can be prepared by conventional techniques, as are described in *Remington's Pharmaceutical Sciences*, a standard reference in this field [Gennaro A R, Ed. *Remington: The Science and Practice of Pharmacy*. 20th Edition. Baltimore: Lippincott, Williams & Williams, 2000]. For therapeutic purposes, the active components of a single, or a combination therapy application can be combined with one or more adjuvants appropriate to the indicated route of administration. The components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration, the amounts of which are ascertainable by the skilled artisan. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration are well and widely known in the pharmaceutical art and these aspects can also be applied to any of the nutritional or dietary supplements described herein.

While the present invention has been described in some detail for purposes of clarity and understanding, one will appreciate that various changes in form and detail can be made without departing from the true scope of the invention.

EXAMPLES

Example 1. Treatment of Autism Spectrum Disorder

In a double-blind clinical study, 20 subjects are divided into two groups (n=10). Inclusion criteria for the subjects include a diagnosis of an autism spectrum disorder, age<18 years old and low biotin serum levels at study start date. The control group receives a placebo, the trial group receives magnesium biotinate at 10-100 mg/day for 12 weeks. Biotin serum levels, carboxylase levels from peripheral blood mononuclear cells, and magnesium serum levels can be measured at baseline and at week 4, 8 and 12. Intellectual abilities, behavior, quality of life, developmental age, nonverbal intellectual ability and other measures of autism symptoms can be assessed at baseline and at week 4, 8 and 12. After week 12, both groups can receive the magnesium biotinate. Further assessment of intellectual abilities, behavior, quality of life, developmental age, nonverbal intellectual ability and other measures of autism symptoms can be conducted every 4 weeks.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

When introducing elements of the present application or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present disclosure to its fullest extent. The specific embodiments are, therefore, to be construed as merely illustrative, and not limitative of the remainder of the disclosure in any way whatsoever. While the present disclosure has been described in some detail for purposes of clarity and understanding, one will appreciate that various changes in form and detail can be made without departing from the true scope of the application.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of treatment comprising assessing the biotin status of an individual with an autism spectrum disorder and subsequently providing magnesium biotinate in an amount between 10 mg/day to 1000 mg/day, to the individual to treat the autism spectrum disorder.

2. The method of claim 1, wherein the assessing the biotin status of the individual with an autism spectrum disorder comprises obtaining samples from the individual and testing for markers associated with biotin deficiency.

3. The method of claim 2, wherein the samples are obtained from blood, serum, peripheral blood mononuclear cell (PBMC), saliva, urine, feces or sweat from the individual with an autism spectrum disorder.

4. The method of claim 2, wherein the samples are tested for markers indicative of impaired carboxylases.

5. The method of claim 4, wherein the samples are tested for impaired propionyl-CoA carboxylase (PCC) or pyruvate carboxylase (PC).

6. The method of claim 5, wherein the samples are tested for amino acids found at abnormal levels due to impaired PCC or PC or other carboxylase.

7. The method of claim 2, wherein the samples are tested for biotin, propionic acid, pyruvate, or lactate.

8. The method of claim 2, wherein the samples are tested for isoleucine, methionine, threonine, and valine.

9. The method of claim 2, wherein the samples are tested for ratios of one amino acid over another.

10. The method of claim 2, wherein the samples are tested for white blood cell count.

11. The method of claim 2, wherein the samples are tested for mitochondrial function.

12. A method of treating an autism spectrum disorder comprising administering magnesium biotinate in an amount between 10 mg/day to 1000 mg/day, to an individual diagnosed with an autism spectrum disorder.

13. The method of claim 12, wherein the type of autism spectrum disorder to be treated is related to low biotin levels, impaired carboxylase function, increased propionic acid levels, or increased levels of isoleucine, methionine, threonine, and/or valine.

14. The method of claim 12, wherein the magnesium biotinate can be provided as a drug, supplement, medical food, food or biologic.

* * * * *